(12) United States Patent
Tan et al.

(10) Patent No.: US 10,918,837 B2
(45) Date of Patent: Feb. 16, 2021

(54) SAFETY NEEDLE ASSEMBLIES AND RELATED METHODS

(71) Applicant: B. BRAUN MELSUNGEN AG, Melsungen (DE)

(72) Inventors: Soo Yong Tan, Penang (MY); Kevin Woehr, Felsberg (DE)

(73) Assignee: B. Braun Melsungen AG, Melsungen (DE)

(*) Notice: Subject to any disclaimer, the term of this patent is extended or adjusted under 35 U.S.C. 154(b) by 0 days.

(21) Appl. No.: 14/536,252

(22) Filed: Nov. 7, 2014

(65) Prior Publication Data
US 2015/0151085 A1    Jun. 4, 2015

Related U.S. Application Data

(60) Provisional application No. 61/911,870, filed on Dec. 4, 2013.

(51) Int. Cl.
*A61M 25/06* (2006.01)
*A61M 5/32* (2006.01)
*A61M 25/00* (2006.01)

(52) U.S. Cl.
CPC ........ *A61M 25/0618* (2013.01); *A61M 5/321* (2013.01); *A61M 5/3202* (2013.01);
(Continued)

(58) Field of Classification Search
CPC .......... A61M 39/0693; A61M 25/0097; A61M 25/0693; A61M 5/1626; A61M 5/3202;
(Continued)

(56) References Cited

U.S. PATENT DOCUMENTS

| | | | | |
|---|---|---|---|---|
| 5,344,408 A | * | 9/1994 | Partika | ................ A61M 5/3273 604/192 |
| 6,203,527 B1 | * | 3/2001 | Zadini | ................ A61M 5/3273 604/110 |

(Continued)

FOREIGN PATENT DOCUMENTS

| | | |
|---|---|---|
| CN | 1547493 A | 11/2004 |
| CN | 101610809 A | 12/2009 |

(Continued)

OTHER PUBLICATIONS

Office Action with Search Report on corresponding foreign application (RU Application No. 2016126443) from the Russian Intellectual Property Office dated May 8, 2018.

(Continued)

*Primary Examiner* — Bhisma Mehta
*Assistant Examiner* — William R Frehe
(74) *Attorney, Agent, or Firm* — Klein, O'Neill & Singh, LLP

(57) ABSTRACT

A safety needle assembly having a first hub attached to a flexible tube and a second hub attached to a needle projecting through the flexible tube. A needle guard is positioned in an interior cavity of the first hub. The needle guard has a proximal wall having an opening and two arms each with an end and wherein the two ends spaced from and biased toward the needle in a ready position. In a particular example, a support is located inside the cavity of the first hub and wherein the two ends of the two arms on the needle guard rest on the support in the ready position.

9 Claims, 6 Drawing Sheets

(52) U.S. Cl.
CPC ........ *A61M 5/3205* (2013.01); *A61M 5/3273* (2013.01); *A61M 25/0097* (2013.01); *A61M 25/0606* (2013.01); *A61M 25/0631* (2013.01); *A61M 25/0612* (2013.01); *A61M 25/0693* (2013.01); *A61M 2005/3247* (2013.01)

(58) Field of Classification Search
CPC .............. A61M 5/321; A61M 25/0612; A61M 25/0618; A61M 25/0625; A61M 25/0631; A61M 5/3205; A61M 5/3269
See application file for complete search history.

(56) References Cited

U.S. PATENT DOCUMENTS

| | | | |
|---|---|---|---|
| 6,585,704 B2 | 7/2003 | Luther et al. | |
| 6,616,630 B1 | 9/2003 | Woehr et al. | |
| 7,500,965 B2 | 3/2009 | Menzi et al. | |
| 7,530,965 B2* | 5/2009 | Villa .................. | A61M 5/3273 604/110 |
| 7,534,231 B2 | 5/2009 | Kuracina et al. | |
| 7,731,687 B2 | 6/2010 | Menzi et al. | |
| 7,731,692 B2 | 6/2010 | Moos et al. | |
| 7,850,650 B2 | 12/2010 | Breitweiser | |
| 8,273,056 B2 | 9/2012 | Kuracina et al. | |
| 8,308,691 B2 | 11/2012 | Woehr et al. | |
| 8,419,687 B2 | 4/2013 | Moos et al. | |
| 8,591,467 B2* | 11/2013 | Walker .............. | A61M 25/0618 604/164.08 |
| 8,672,895 B2 | 3/2014 | Kuracina et al. | |
| 8,764,711 B2 | 7/2014 | Kuracina et al. | |
| 8,821,439 B2 | 9/2014 | Kuracina et al. | |
| 2002/0169418 A1 | 11/2002 | Menzi et al. | |
| 2006/0155245 A1* | 7/2006 | Woehr .............. | A61M 39/0693 604/164.08 |
| 2007/0112305 A1* | 5/2007 | Brimhall ........... | A61M 25/0606 604/164.08 |
| 2008/0108944 A1 | 5/2008 | Woehr et al. | |
| 2008/0249478 A1* | 10/2008 | Ishikura ............ | A61M 25/0618 604/198 |
| 2009/0259201 A1* | 10/2009 | Hwang .............. | A61B 5/15003 604/263 |
| 2010/0249707 A1 | 9/2010 | Woehr et al. | |
| 2011/0213307 A1* | 9/2011 | Kawai ................... | A61M 5/158 604/164.08 |
| 2011/0251517 A1* | 10/2011 | Swisher ............... | A61B 10/025 600/567 |
| 2012/0172806 A1* | 7/2012 | Woehr .............. | A61M 25/0631 604/164.08 |
| 2012/0220956 A1 | 8/2012 | Kuracina et al. | |
| 2013/0023826 A1 | 1/2013 | Ishida | |
| 2013/0023835 A1 | 1/2013 | Kuracina et al. | |
| 2013/0030370 A1 | 1/2013 | Walker et al. | |
| 2013/0138015 A1* | 5/2013 | Kuracina .......... | A61M 25/0625 600/576 |
| 2014/0025009 A1 | 1/2014 | Erskine | |

FOREIGN PATENT DOCUMENTS

| | | |
|---|---|---|
| CN | 103402567 A | 11/2013 |
| EP | 2638926 | 9/2013 |
| JP | 2002-325847 A | 11/2002 |
| JP | 2005-531377 A | 10/2005 |
| RU | 151553 U1 | 4/2015 |
| WO | WO 2011/038931 A1 | 4/2011 |
| WO | WO 2012/139034 | 10/2012 |
| WO | WO 2013/021350 | 2/2013 |

OTHER PUBLICATIONS

Office Action on corresponding foreign application (EP Application No. 14 806 282.1) from the European Patent Office dated Jun. 11, 2019.
First Office Action and Search Report on corresponding foreign application (CN Application No. 201480074914.0) from the Chinese National Intellectual Property Administration dated Mar. 8, 2019.
Office Action on corresponding foreign application (JP Application No. 2016-536113) from the Japanese Patent Office dated Dec. 4, 2018.
Office Action on corresponding foreign application (RU Application No. 2016126443) from the Russian Patent Office dated Nov. 9, 2018.
Substantive Examination Adverse Report including Search Report on corresponding foreign application (MY Application No. PI 2016702014) from the Intellectual Property Corporation of Malaysia, dated Oct. 1, 2019.
Office Action on corresponding foreign application (CN Application No. 201480074914.0) from the National Intellectual Property Administration, P.R. China, dated Aug. 2, 2019.
Decision on Rejection on corresponding foreign application (CN Application No. 201480074914.0) from the National Intellectual Property Administration, P.R. China, dated Jan. 3, 2020.
Search Report and Written Opinion on corresponding foreign application (SG Application No. 10201804744V) from the Intellectual Property Office of Singapore (IPOS), dated Mar. 20, 2020.
Office Action on corresponding foreign application (JP Application No. 2019-123389) from the Japanese Patent Office, dated Jul. 7, 2020.
Examination Report on corresponding foreign application (AU Application No. 2014359257) from the Australian Patent Office dated Aug. 28, 2018.

* cited by examiner

SAFETY NEEDLE ASSEMBLIES AND RELATED METHODS

FIELD OF ART

The present invention is generally directed to needle safety assemblies and related methods and more particularly to needle safety assemblies and related methods utilizing needle guards having unique mounting for low friction between the needle guard and the needle during needle movement, such as during retraction of the needle relative to the needle guard.

BACKGROUND

Insertion procedure for an intravenous (IV) catheter assembly contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand to stop the flow of blood through the catheter; and (4) the healthcare worker then tapes the exposed end of the catheter (the catheter hub) to the patient's skin and connects it to the source of the fluid to be administered into the patient's vein.

One problem is that, immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick, which, under the circumstances, leaves the healthcare worker vulnerable to the transmission of various dangerous blood-borne pathogens, including AIDS and hepatitis.

Other needle types similarly expose healthcare workers to risks of accidental needle sticks. For example, a doctor administering an injection, using a straight needle, a Huber needle, an epidural needle, etc., may place the used needle on a tray for subsequent disposal by a nurse. For the period between placing the used needle on a tray or a work station to the time it is discarded, the used needle is a potential source for disease transmissions for those that work near or around the needle.

SUMMARY

The various embodiments of a needle assembly have several features, no single one of which is solely responsible for their desirable attributes. Without limiting the scope of the present embodiments as set forth in the claims that follow, their more prominent features now will be discussed briefly.

Aspects of the present disclosure include an indwelling needle assembly that includes a first hub, a flexible tube attached to a distal end of the first hub, a second hub connected to a proximal end of the first hub, a needle attached to the second hub and projecting through the flexible tube, and a needle guard positioned in an interior cavity of the first hub, the needle guard comprising a proximal wall having an opening and two arms each comprising an end located opposite the proximal wall, the two ends being biased away from and spaced from the needle in a ready position, and the needle passing through the opening of the needle guard.

The indwelling needle can further include a support located inside the interior cavity of the first hub wherein the two ends of the two arms on the needle guard rest against the support in the ready position.

The support can be ring shaped and coaxially disposed with the flexible tube. The support can also be a projection protruding from a distal surface of the interior cavity of the first hub. Each of the two ends of the two arms can have a sharp end contacting the support. The two arms of the needle guard can cross each other to form an intersection or a cross-section, and the needle further passes through the cross-section.

The needle can include a needle tip and a change in profile located proximal of the needle tip. When the change in profile abuts against the proximal wall of the needle guard and the ends of the arms no longer bias against the support, the two arms close over the needle tip in a needle protective position.

The indwelling needle can further include a guide arm attached to the first hub, wherein the guide arm is configured for pressing against the flexible tube. The guide arm can include a guide section configured to press against the flexible tube and a contact flange extending from the guide section. The guide arm can be pivotably attached to the first hub.

Another aspect of the present disclosure includes a safety catheter assembly that includes a catheter hub comprising a valve and a valve opener for opening the valve, a catheter tube attached to the catheter hub, a needle hub, a needle attached to the needle hub and projecting through the catheter tube, and a needle guard positioned in an interior cavity of the catheter hub or an interior cavity of a third hub located proximally of the catheter hub. The needle guard can include a proximal wall having an opening and two arms each comprising an end and wherein a support formed with the catheter hub, the third hub, or a valve opener located inside the catheter hub spaces the two ends of the needle guard from the needle in a ready position.

The safety catheter assembly can further include a support located inside the cavity of the third hub wherein the two ends of the two arms on the needle guard rest on the support in the ready position. The support can be ring shaped and coaxially disposed with the flexible tube. The support can be located in the interior cavity of the catheter hub in which the two ends of the two arms on the needle guard rest on the support. The support can also be formed with the valve opener.

The third hub can include a distal wall and at least one arm extending from the distal wall engaged with the catheter hub to retain the third hub in the ready position. The third hub can include two arms engaged with a holding portion of the catheter hub.

The two arms of the needle guard can cross each other to form an intersection or a cross-section. The needle can further pass through the cross-section. Alternatively the two arms can run along side the needle in a ready position and do not intersect. The guard can have end walls that overlap when in a protective position over the needle without also incorporating intersecting arms.

The needle can include a needle tip and a change in profile located proximal of the needle tip. When the change in profile abuts against the proximal wall of the needle guard, the ends of the arms of the needle guard are no longer biasing against the support in a protective position.

The third hub can include a distal wall and an opening defined through the distal wall of the third hub. The distal wall can abut against the catheter hub, with the support centered around the opening of the distal wall of the third hub and extending proximally into a chamber of the third housing. The needle can pass through the opening of the distal wall of the third hub.

The third hub can further include a proximal wall and a sidewall or sidewalls extending between the distal wall of the third hub and the proximal wall of the third hub. The proximal wall of the third hub can define an opening. The needle can pass through the opening of the distal wall of the third hub. The distal wall, the sidewall, and the proximal wall of the third hub can cooperatively define an interior cavity. The needle guard can be positioned in the interior cavity.

The valve can include a plurality of slits or one slit and the valve opener at least one leg.

Yet another aspect of the present disclosure includes a safety catheter assembly including a catheter tube attached to a catheter hub, a needle attached to a needle hub and projecting through the catheter tube and the catheter hub and a needle guard positioned in an interior cavity of the catheter hub and comprising a proximal wall having an opening and two arms each comprising an end biased away from and spaced from the needle and supported by a support located in the interior cavity of the catheter hub in a ready position.

The support can be near a bore at a distal end of the catheter hub. The support can be provided on a valve opener located inside the catheter hub. The valve opener can be sized and shaped to open a valve comprising at least one slit.

Still yet another aspect of the present disclosure includes a method of reducing resistance on a needle of a catheter assembly. The method includes retracting the needle in a proximal direction through a needle guard and a catheter tube attached to a catheter hub. The needle guard has a proximal wall having a proximal opening and two arms each comprising an end. A needle tip of the needle extends out a distal end of the catheter tube prior to retracting.

The method can further include abutting a change in profile of the needle against the proximal wall. For example, when a change in profile abuts the proximal wall, it can abut a perimeter defining a proximal opening of the proximal wall. The proximal wall prevents the change in profile from passing therethrough.

The method can further include covering the needle tip of the needle with at least one end of the arms of the needle guard.

The method can further include a support formed with the catheter hub, a third hub, or a valve opener located inside the catheter hub that spaces the two ends of the needle guard from the needle in a ready position.

The needle can further project through a valve in the catheter hub, and a valve opener in the catheter hub. The valve opener can be configured to press against the valve to open the valve.

The needle guard can be positioned in an interior cavity of the catheter hub or located proximally of the catheter hub or partially in the catheter hub and partially proximal of the catheter hub.

The ends of the arms are supported by a support to prevent the ends from pressing against the needle in the ready position.

A yet further aspect of the present disclosure includes a safety catheter assembly comprising: a catheter hub comprising a valve and a valve opener for opening the valve; a catheter tube attached to the catheter hub; a needle hub; a needle attached to the needle hub and projecting through the catheter tube; a needle guard positioned in an interior cavity of the catheter hub or an interior cavity of a third hub located proximally of the catheter hub; wherein the needle guard comprises a proximal wall having an opening and two arms each comprising an end and wherein the two ends are spaced from and biased toward the needle in a ready position; and wherein a support formed with the catheter hub, the third hub, or a valve opener located inside the catheter hub biases the two ends of the needle guard apart in the ready position.

A still yet further aspect of the present disclosure includes a method of reducing resistance on a needle of a catheter assembly. In an example, the method comprises: retracting the needle held with a needle hub in a proximal direction through a needle guard and a catheter tube attached to a catheter hub, the needle guard comprising a proximal wall having a proximal opening and two arms each comprising an end spaced from and biased towards the needle in a ready position, a needle tip of the needle extending out a distal end of the catheter tube prior to retracting; abutting a change in profile of the needle against the proximal opening on the proximal wall, the proximal opening of the proximal wall preventing the change in profile from passing therethrough; covering the needle tip of the needle with at least one end of the arms of the needle guard in a protective position; and wherein a support formed with the catheter hub, a third hub, or a valve opener located inside the catheter hub biases the two ends of the needle guard apart in the ready position.

Yet another feature of the present disclosure includes a safety catheter assembly comprising: a catheter hub comprising a valve and a valve opener for opening the valve; a catheter tube attached to the catheter hub; a needle hub; a needle attached to the needle hub and projecting through the catheter tube; a needle guard positioned in an interior cavity of the catheter hub or an interior cavity of a third hub located proximally of the catheter hub; wherein the needle guard comprises a proximal wall having an opening and two arms each comprising an end; and wherein a support biases the two ends of the needle guard away from the needle in a ready position and the support is spaced from the proximal opening of the proximal wall in the ready position and a protective position.

Yet another aspect of the present disclosure includes a method of reducing resistance on a needle of a catheter assembly comprising: retracting the needle held with a needle hub in a proximal direction through a needle guard and a catheter tube attached to a catheter hub, the needle guard comprising a proximal wall having a proximal opening and two arms each comprising an end, a needle tip of the needle extending out a distal end of the catheter tube prior to retracting; abutting a change in profile of the needle against the proximal opening on the proximal wall, the proximal opening of the proximal wall preventing the change in profile from passing therethrough; covering the needle tip of the needle with at least one end of the arms of the needle guard in a protective position; and wherein a support biases the two ends of the needle guard away from the needle in a ready position and the support is spaced from the proximal opening of the proximal wall in the ready position and the protective position.

BRIEF DESCRIPTION OF THE DRAWINGS

These and other features and advantages of the present devices, systems, and methods will become appreciated as the same becomes better understood with reference to the specification, claims and appended drawings wherein:

DETAILED DESCRIPTION

The detailed description set forth below in connection with the appended drawings is intended as a description of the presently preferred embodiments of safety needle assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
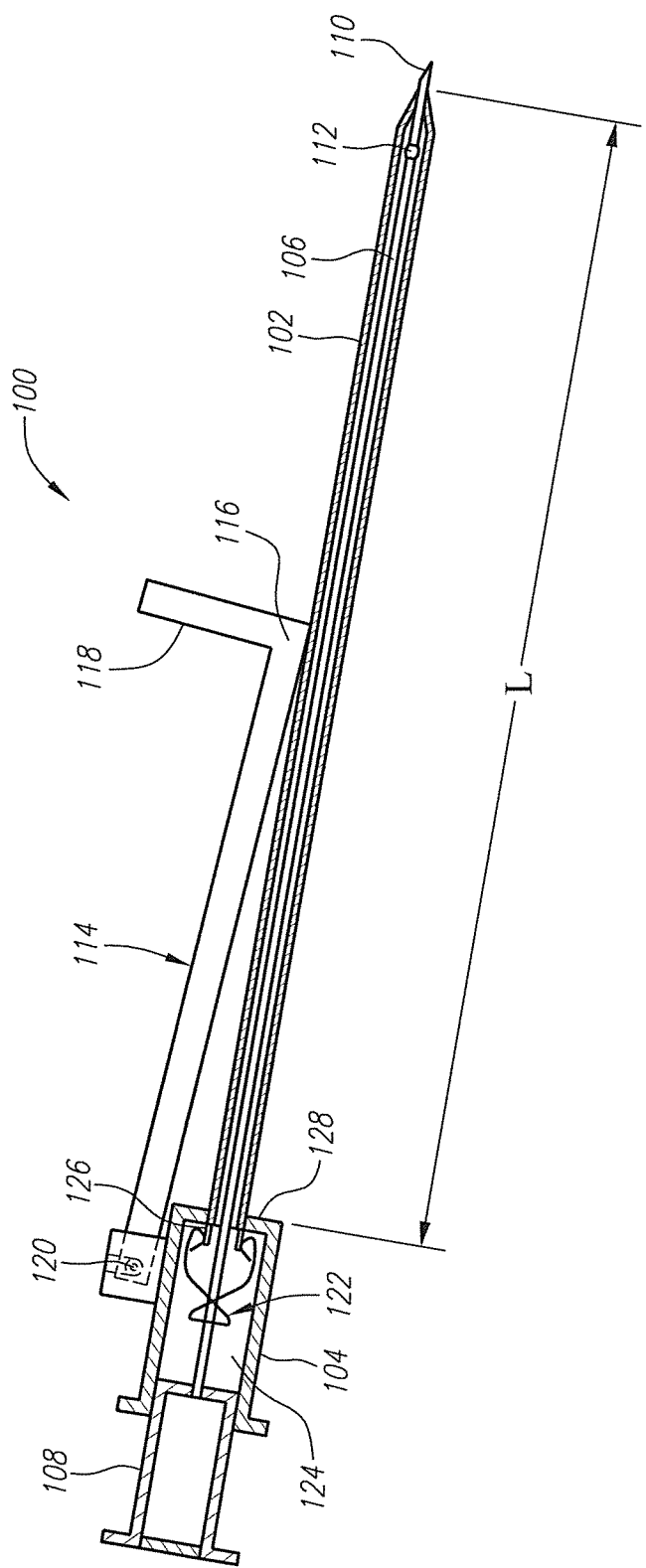
FIG. 1 is a schematic cross-sectional side view of one embodiment of a safety needle assembly having a guide arm.

FIG. 1 is a schematic cross-sectional side view of one embodiment of a safety needle assembly 100 provided in accordance with aspects of the present disclosure, which in the present embodiment is an indwelling needle. As shown, the needle assembly 100 comprises an outside flexible tube 102 attached to a first hub 104 and a needle 106 disposed internally of the flexible tube 102 and attached to a second hub 108. The needle 106 may be hollow, such as having a lumen, or solid, such as a stylet, and can be made of a metal or other biocompatible material. The needle has a needle tip 110 and a change in profile 112, such as a needle bulge or crimp, located proximally of the needle tip 110. The second hub 108 can be removably coupled to the first hub 104, but is preferably only in abutting contact and not friction fit inside the female Luer taper of the first hub 104.

The safety needle assembly 100 may be used as a peripheral vein catheter and therefore normally has a length L of up to about 50.0 cm. At this length, the flexible tube 102 and the needle 106 can flex or bend when attempting to perform a medical procedure by pushing on the first hub 104, the second hub 108, or both. Thus, a guide arm 114 is provided having a guide section 116 and a contact flange 118 to facilitate the process. The guide section 116 is configured to press against the outer tube 102 while a finger may push against the contact flange 118 to steady the insertion during the medical procedure.

The guide arm 114 can be pivotably connected to the first hub 104 at the pivot connection point 120. As the needle 106 and tube 102 penetrate the vein, the guide arm 114 can rotate in a direction (shown in FIG. 1 as counter-clockwise) to provide the necessary clearance for the insertion. After successful catheterization, the second hub 108 and the needle 106 are retracted away from the first hub 104 and the tube 102.

A tip protector or needle guard 122 can be provided in the interior cavity 124 of the first hub 104. The interior cavity is further provided with a support 126. In the present embodiment, the support 126 can embody a ring, which is coaxially disposed with the flexible tube 102. In one example, the support 126 is attached to the interior of the first hub 104 to provide a support surface for the needle guard 122, as further discussed below. In another example, the support 126 is a molded projection, such as a rib, on the interior of the first hub 104. Further, instead of a continuous or complete ring, the support 126 may embody two or more separate sections, such as two or more ribs, formed around the bore inlet 128 to the tube 102. The support 126 can be any structure so long as it does not interfere with the needle 106 passing through and can provide a support surface for the needle guard 122.

Figure 2A:
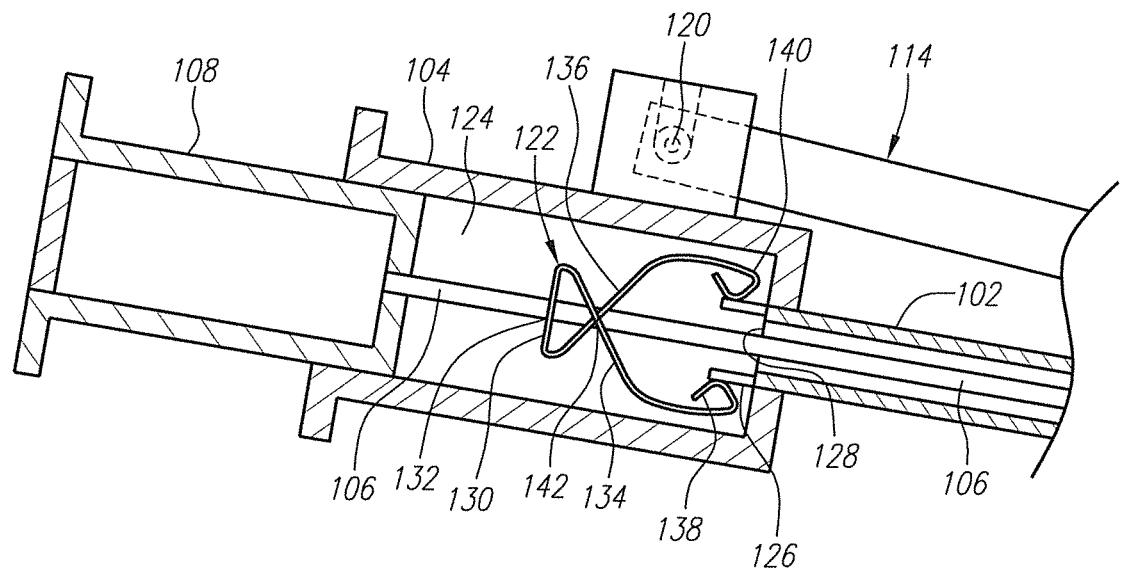
FIG. 2A is a close up view of the assembly of claim 1 showing a needle guard located inside a cavity of a first hub of the safety needle assembly of FIG. 1.

With reference now to FIG. 2A, the needle guard 122 is shown disposed in the interior cavity 124 of the first hub 104. The needle guard 122 comprises a proximal wall 130 comprising a proximal opening 132 having the needle passing therethrough and two arms 134, 136 each having an end 138, 140 biasing against the support 126 in the ready position in which the needle is ready for use on a patient. The two arms 134, 136 can have the same length or different lengths so that the two ends are staggered axially. Each end 138, 140 can comprise a curved section having a relatively smooth surface for biasing against or contacting the support 126 so as to avoid biasing the support with a sharp edge. In other examples, the ends 138, 140 contact the support 126 by way of a sharp end edge, which is less preferred. The needle guard 122 can be made of a metal or other biocompatible material, such as plastics or a combination of metal and plastic.

In one embodiment, the needle guard 122 and the needle 106 only contact one another, if at all, at the proximal opening 132 of the proximal wall 130. In another embodiment, the needle guard 122 and the needle 106 can also contact each other, if at all, at the cross-section or intersection 142 of the two arms. Thus, during retraction of the needle 106 from the flexible tube 102, the only drag experienced or felt, if at all, by the user as the needle is retracted away is at the opening 132 of the proximal wall. The two ends 138, 140 are spaced from the needle 106, such as by a gap or space or the support 126, during most if not all of the retraction of the needle 106 away from the flexible tube 102 and first hub 104.

Figure 2B:
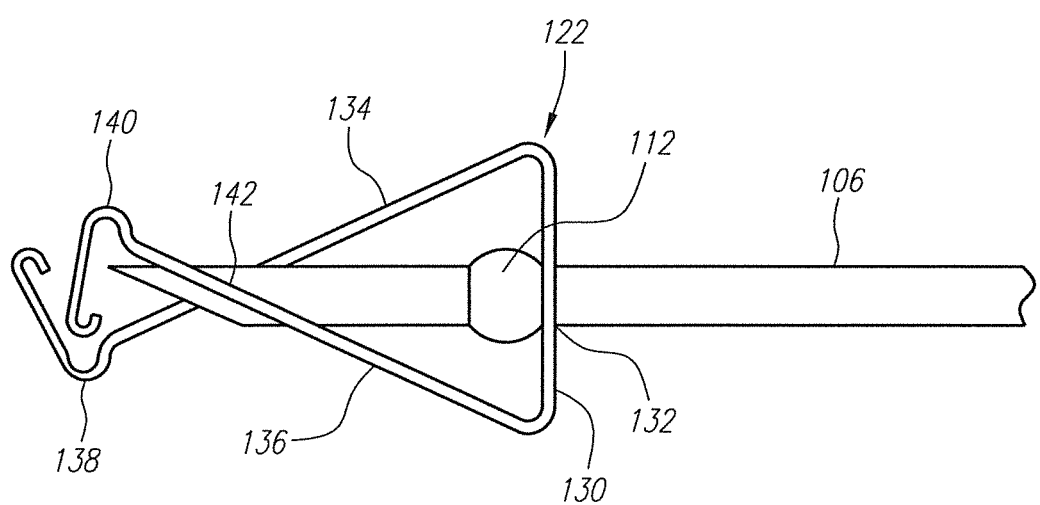
FIG. 2B shows a needle guard protecting the needle tip of the needle.

During removal of the needle 106 away from the first hub 104, the change in profile 112 near the needle tip 110 eventually abuts the perimeter of the proximal opening 132 of the needle guard. Because the change in profile 112 is physically larger than the perimeter of the proximal opening 132 on the needle guard at least along the cross-section, the crimp will engage the opening 132 and will pull the needle guard 122 out of the cavity 124 of the first hub 104 upon retraction of the second hub 108 and the needle 105 away from the first hub 104. It is understood that when the crimp or change in profile engages the opening on the proximal wall, it actually engages a perimeter defining the proximal opening, or more broadly engages the proximal wall of the needle guard which has the opening. As the needle guard 122 moves in the proximal direction with the needle change in profile 112 engaged to the proximal wall 130, the ends 138, 140 of the two arms 134, 136 on the needle guard 122 slide proximally off of the support 126 to close over the needle tip 110 to prevent inadvertent needle sticks with the sharp tip. FIG. 2B illustrates the change in profile 112 contacting the opening 132 at the proximal wall 130 and the two ends 138, 140 overlap just distal of the needle tip 110. Alternatively only one arm has the curved end to block the distal path of the needle tip 110.

Thus, aspects of the present disclosure is understood to include an indwelling needle assembly comprising a first hub attached to a flexible tube and a second hub attached to a needle projecting through the flexible tube. A needle guard is positioned in an interior cavity of the first hub. Wherein the needle guard comprises a proximal wall having an opening and two arms each comprising an end and wherein the two ends are spaced from the needle in a ready position and are in tension so as to bias towards the needle. In a particular example, a support is located inside the cavity of the first hub and wherein the two ends of the two arms on the needle guard rest on the support in the ready position. Thus, upon retraction of the needle and until a change in profile on the needle engages the proximal wall of the needle guard and pulls the proximal wall in a proximal direction which then pulls the two arms from the support, contact between the needle and the needle guard is minimized.

In an example, the indwelling needle assembly discussed with reference to FIGS. 1 and 2 and be adopted for use with a safety intravenous catheter. For example, the first hub can be a catheter hub attached to a catheter tube and the second hub can be a needle hub attached to a needle projecting through the catheter tube. The guide arm of FIG. 1 can be omitted. A needle guard is positioned in an interior cavity of the catheter hub. Wherein the needle guard comprises a proximal wall having an opening and two arms each comprising a distal end and wherein the two distal ends are spaced from the needle in a ready position inside the catheter hub. The two arms are resilient and therefore bias toward the needle. In a particular example, a support is located inside the cavity of the catheter hub and wherein the two ends of the two arms on the needle guard rest on the support in the ready position so that they are spaced from the needle shaft. Thus, upon retraction of the needle and until a change in profile on the needle engages the proximal wall of the needle guard and pulls the proximal wall in a proximal direction which then pulls the two arms from the support, contact between the needle and the needle guard is minimized.

A further aspect of the present disclosure is understood to include a support formed with a catheter hub, a third hub (as shown with reference to FIG. 3), or a valve opener located inside the catheter hub (as shown with reference to FIGS. 4-11) that spaces the two ends 138, 140 of the needle guard 122 from the needle 158, such as away from the needle so that the ends do not touch the needle in a ready position. As the support 126 is formed with the catheter hub, the third hub, or the valve opener, the support is spaced from the proximal opening 132 of the proximal wall of the needle guard in both a ready position, as shown in FIG. 2A, and in a protective position, as shown in FIG. 2B. In FIG. 2B, the support 126 is located with the first hub and is therefore spaced from the proximal opening 132 of the proximal wall of the needle guard. Still further, as the support 126 is formed with the catheter hub, the third hub, or the valve opener, the support is spaced from the proximal opening 132 of the proximal wall of the needle guard in both a ready position, as shown in FIG. 2A, and in a protective position, as shown in FIG. 2B, and spaced from the needle guard in the protective position. In FIG. 2B, the support 126 is located with the first hub and is therefore spaced from the proximal opening 132 of the proximal wall of the needle guard as well as the entire needle guard.

For other safety needle assemblies and safety needle assembly components disclosed herein below, it is understood that where a feature is shown but not expressly described and is otherwise the same or similar to the feature or features described elsewhere, such as above with reference to FIGS. 1 and 2, the disclosed part or parts shown in the subsequent drawing figures but not expressly described because of redundancy and because knowledge is built on a foundation laid by earlier disclosures may nonetheless be understood to be described or taught by the same or similar features expressly set forth in the text for the embodiments in which the feature or features are described, such as for the safety needle assembly of FIGS. 1 and 2. Said differently, subsequent disclosures of the present application are built upon the foundation of earlier disclosures unless the context indicates otherwise. The disclosure is therefore understood to teach a person of ordinary skill in the art the disclosed embodiments and the features of the disclosed embodiments without having to repeat similar components and features in all embodiments since a skilled artisan would not disregard similar structural features having just read about them in several preceding paragraphs nor ignore knowledge gained from earlier descriptions set forth in the same specification. As such, the same or similar features shown in the following safety needle assemblies incorporate the teachings of earlier embodiments unless the context indicates otherwise. Therefore, it is contemplated that later disclosed embodiments enjoy the benefit of earlier expressly described embodiments, such as features and structures of earlier described embodiments, unless the context indicates otherwise.

Figure 3:
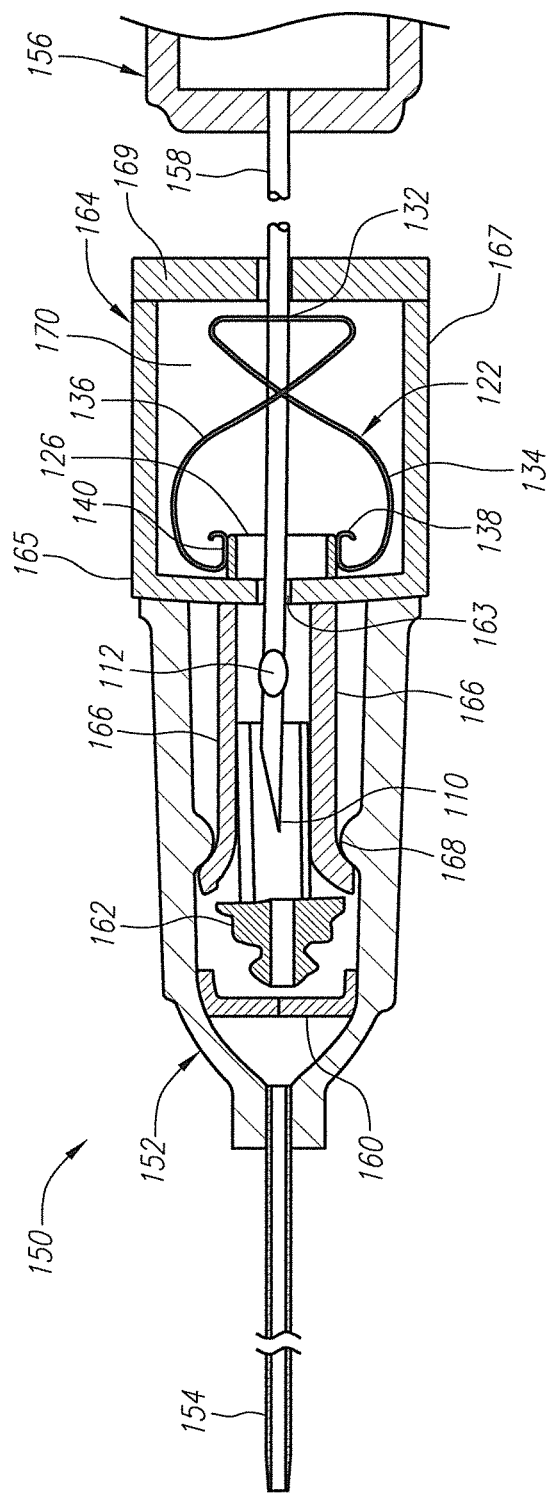
FIG. 3 is a schematic cross-sectional view of another embodiment of a safety IV catheter assembly having a needle guard located in another embodiment of a third hub.

With reference now to FIG. 3, a safety IV catheter 150 comprises a first hub or catheter hub 152 having a catheter tube 154 attached thereto, and a second hub or needle hub 156 having a needle 158 attached thereto and extending partially through the catheter hub 152. As shown, the needle 158 is in the process of being removed from the catheter hub 152, such as following successful venipuncture. The safety IV catheter 150 can further comprise a valve 160 positioned at a distal end of an interior of the catheter hub 152, a valve opener 162 positioned proximally of the valve 160, and a third hub 164, which can also be referred to as a third housing or a guard housing, positioned proximally to the catheter hub 152. The third hub 164 can couple directly to the catheter hub 152, such as having a Luer projection for frictionally engaging the female Luer of the catheter hub 152. The valve 160 can be any check valve configured to prevent fluid or blood from leaking proximally out of the catheter hub. The needle 158 can pass through the valve 160 in a ready position, such as through one or more slits provided centrally of the valve.

The valve opener 162 is configured to press against the valve 160 and open the valve 160 to allow fluid or solution to pass distally through the catheter hub 152 and the catheter tube 154. For example, the valve opener 162 can be advanced distally by a male medical implement, such as a syringe tip, which presses against the proximal end of the valve opener 162 to push the nose section of the valve opener distally forward into the valve to open, such as by opening one or more slits. In one example, the valve opener 162 has a wedge shape nose section to press open the valve 160 and an extension or leg 1622 to be pushed against by a male medical implement. Although a single extension or leg 1622 is usable to push the valve opener, two or more extensions are preferred. The extension 1622 can be one or more separate sections that can be pressed against by a male medical implement to advance the valve opener 162 against the valve 160. The valve opener 162 has an opening 1620 defined through a center of the nose section of the valve opener 162 for the needle 158 to pass therethrough.

The third hub 164 has a sidewall 167 extending from the distal wall 165 and a proximal wall 169 such that the sidewall 167 extends between the distal wall 165 and the proximal wall 169 of the third hub 164. The proximal wall 169 of the third hub 164 has an opening for the needle 158 to pass therethrough. The needle 158 also passes through the opening 163 of the distal wall 165 of the third hub 164. The distal wall 165, the sidewall 167, and the proximal wall 169 of the third hub 164 cooperatively define an interior cavity or space 170 having a needle guard 122 disposed therein. The shape of the third hub 164 can be hemispherical, cylindrical, rectangular, polygonal, or irregular shaped, so long as the needle 158 can pass through the proximal wall 169 and the distal wall 165, and the needle guard 122 can fit inside the interior cavity 170 of the third hub 164. In other words, side wall 167 can be made up of multiple portions each having their own plane. Accordingly the sidewall 167 can be cylindrical, rectangular, polygonal, or irregular shaped. In one example, the sidewall 167 is unitarily formed to the distal wall 165 and the proximal wall is separately formed and subsequently attached to the sidewall after the needle guard 122 is placed inside the interior cavity 170. In another embodiment, the sidewall 167 is unitarily formed with the proximal wall 169 and the sidewall is attached to the distal wall 165 after the needle guard 122 is placed into the interior cavity 170.

The third hub 164 can be made of metal, plastic, or a biocompatible material. The distal wall 165 abuts against the catheter hub 152 such that the third hub 164 is positioned between the catheter hub 152 and the needle hub 156. The needle 158 passes through the opening 163 of the distal wall 165 of the third hub 164. The third hub 164 can have at least one arm 166 sized and shaped to engage the catheter hub 152 in the ready position. As shown, two arms 166 extend distally and engage the annular projection or bump 168 inside the catheter hub 152 to retain the third hub 164 to the catheter hub 152 in the ready position and during retraction of the needle 106 following successful venipuncture. The arms 166 and valve opener 162 are sized so as to avoid interference with the operation of each other. The wall 165 can be a circular plate or any other shape that completely covers or partially covers the interior of the catheter hub 152.

A support 126 is provided in the third hub 164. The support 126 can be centered around the opening 163 or near the opening 163 of the distal wall 165 of the third hub 164. As described above for the support 126 of FIG. 2A, the support 126 can embody a ring, which is coaxially disposed with the catheter tube 154. In one example, the support 126 is attached to the third hub 164 to provide a support surface for the needle guard 122. In another example, the support 126 is a molded projection, such as a rib, to the distal wall 165 of the third hub 164. In yet another example, the support 126 is integrally formed with the third hub 164, such as by way of glue or detents. Further, instead of a continuous or complete ring, the support 126 may embody two or more separate sections, such as two or more ribs, formed around the bore inlet 128 to the tube 102. The support 126 can be any structure so long as it does not interfere with the needle 106 passing through and can provide a support surface for the needle guard 122.

The needle guard 122 shown in FIG. 3 is similar to the needle guard of FIG. 2A. The two ends 138, 140 of the two arms are similarly spaced from the needle shaft in the ready position. As shown, the two ends 138, 140 are biased against the support 126 located inside the third hub 164 and are spaced from the needle shaft in the ready position and during retraction of the needle 158 from the catheter hub 152. As previously discussed, when the needle 158 is retracted away from the catheter hub 152, the change in profile 112, such as a needle crimp, abuts a perimeter defining the opening 132 on the proximal wall of the needle guard and the needle guard 122 eventually separates from the support 126 to block the needle tip 110 from inadvertent needle sticks in a similar manner as previously discussed and as shown with reference to FIG. 2B.

Figure 4:
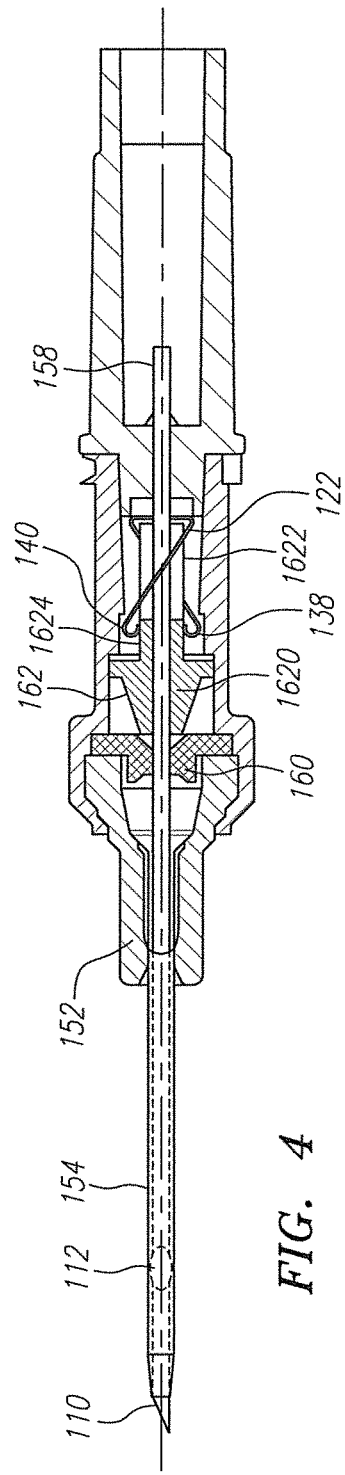
FIG. 4 is a schematic cross-sectional view of a needle assembly coupled to another embodiment of a catheter assembly with a needle guard support on a valve opener.
Figure 5:
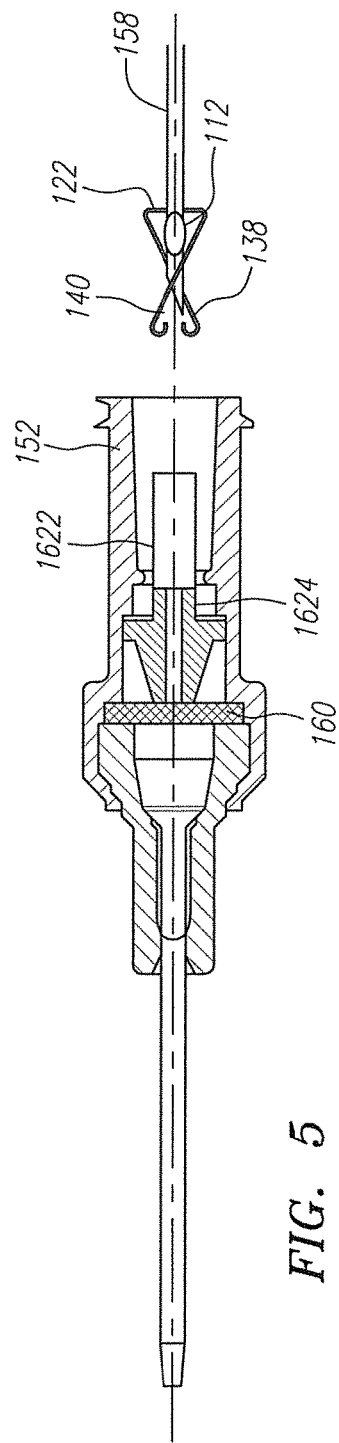
FIG. 5 is a schematic cross-sectional view of the catheter assembly of FIG. 4 with the needle assembly removed.
Figure 6:
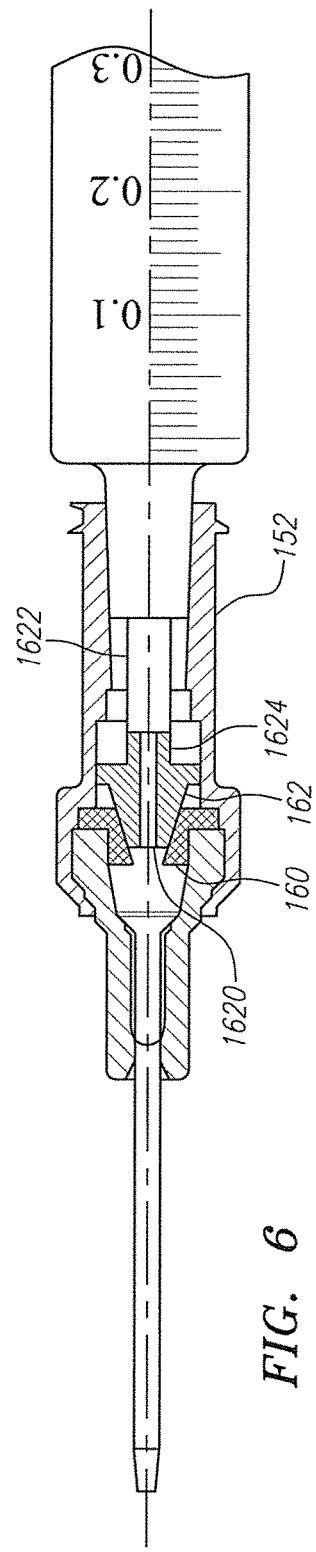
FIG. 6 is a schematic cross-sectional view of the catheter assembly of FIG. 4 coupled with a syringe.

With reference now to FIGS. 4-6, an alternative catheter assembly 150 provided in accordance with further aspects of the present devices, systems, and methods is shown. In the present catheter assembly, a support for the needle guard can be implemented directly with a valve opener 162. Furthermore, the catheter hub 152 can be a single piece or formed from two separate pieces that are attached together. The valve opener 162 can have a support 1624 extending from a proximal end of the nose section of the valve opener 162 to support the needle guard 122. In one embodiment, the support 1624 is a stub having a bore and is shorter in height or width than the width of the extension 1622. The needle guard 122 rests on the valve opener support 1624 until the needle 158 is retracted out of the catheter hub 152 and the needle crimp abuts the opening on the needle guard 122 as discussed above to separate the needle guard from the support 1624 to then block the needle tip 110, similar to that shown in FIG. 2B.

Specifically, the distal ends 138, 140 of the needle guard 122 are shown rested on the support 1624 and the proximal wall 130 of the needle guard 122 is recessed into the interior of the catheter hub and the proximal end most part of the catheter hub is located proximally of the proximal wall 130 so that a nose section of the needle hub 156 can project into the catheter hub 152 without interfering with the extension 1622 or the needle guard 122 in a ready position (FIG. 4). Alternatively the distal portion of the needle hub 156 can extend around the exterior of the proximal end portion of catheter hub or there can be a simple abutment without overlapping of the catheter hub and needle hub. Thus, the height or width of the extension 1622 and the support 1624 can vary so long as the needle hub 156 does not interfere with the needle guard 122 or the extension 1622. The valve opener can be can be made from any biocompatible material. In the three figures shown, the catheter assembly 150 is shown in a ready position in FIG. 4, in a used position shown in FIG. 5, in which the needle guard 122 covers the needle tip of the needle and the valve is closed, and in valve opened position in FIG. 6, in which a male Luer taper of a syringe is inserted into the catheter hub and advances the valve opener distally forward to open the valve.

As shown, the support 1624 can be centered around or located near the opening 1620 through the nose section of the valve opener 162. As described above for the support 126 of FIG. 2A, the support 1624 of the present embodiment can embody many shapes and configurations to support the needle guard 122. The support 1624 can be any structure so long as it does not interfere with the needle 106 passing through the valve opener 162 and can provide a support surface for the needle guard 122. The support 1624 can be a cylindrical ring, such as a stub, or two separate sections. In some examples, the support can incorporate exterior surface features to enable the two ends of the needle guard to easily separate from the support or to make the separation more difficult. For example, the exterior surface can be smooth and can even taper inwardly in the proximal direction to facilitate separation. Alternatively, gripping features, such as bumps or notches, may be incorporated to make the separation between the two ends of the needle guard and the support more difficult by increasing the resistance. The exterior features discussed herein may be incorporated on any of the supports discussed elsewhere herein.

Figure 7:
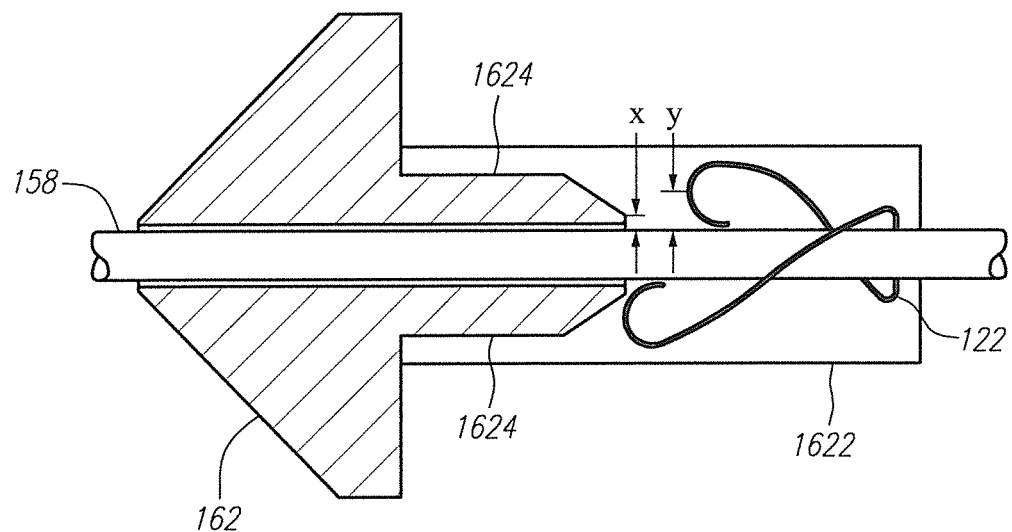
FIG. 7 is a cross-sectional view of one embodiment of the valve opener with the needle guard.
Figure 8:
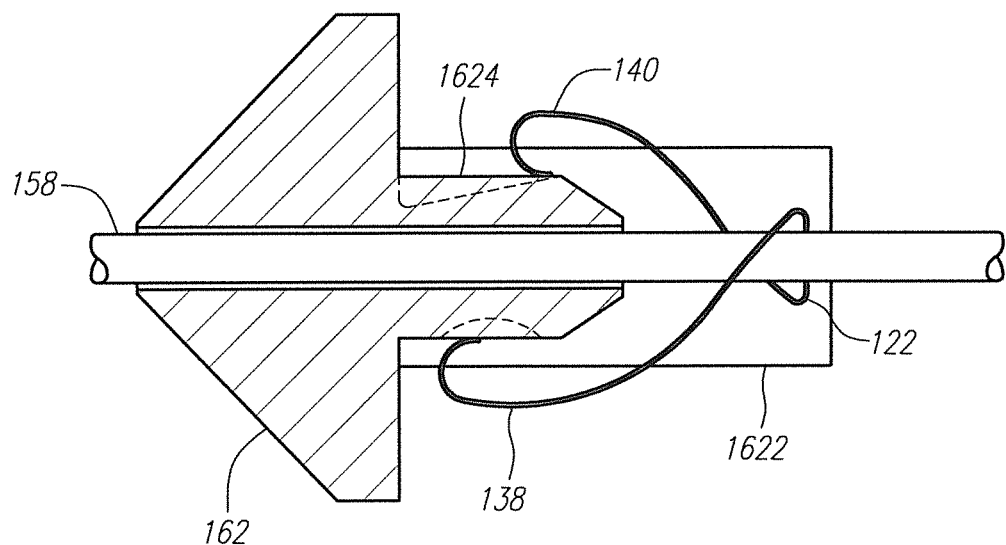
FIG. 8 is a cross-sectional view of one embodiment of the valve opener with the needle guard mounted on a support of the valve opener of FIG. 7.

One method for mounting the needle guard 122 onto the support 1624 comprises a step of sliding the distal end of the needle guard 122 onto the support 1624 of a valve opener 162 so that the two arms 134, 136 are spaced from the needle shaft in the ready position. With reference to FIG. 7, to ensure the needle guard 122 is able to slide onto the support 1624, the distance x between the needle shaft and outer surface of the support 1624 should be less than the distance y between the needle shaft and the transition point of the needle guard 122. The transition point can be the turning point where the curved section of the ends 138, 140 of the needle guard 122 have reached a maximum and begins to curve inward thereby allowing the curved surface of the ends 138, 140 to engage the outer surface of the support 1624 thereby spreading the ends 138, 140 apart from each other away from the needle shaft and biasing against the support 1624. If the distance x between the support 1624 and the needle shaft is greater than the distance y between the needle shaft and the transition point, then the end of the support 1624 can be tapered (as shown in FIGS. 7 and 8) until the distance x between the support 1624 and the needle shaft is less than the distance y between the needle shaft and the transition point. In one embodiment, the outer surface of the support 1624 can be tapered inwardly (as shown in FIG. 8), such as incorporating recessed sections, from the end of the support 1624 towards the main body of the valve opener 162 so that the two ends of the needle guard can settle into the space and be more secured to the support. This helps to prevent the needle guard 122 from unintended premature separation from the support 1624 of the valve opener. In another embodiment, the support 1624 has a groove (as shown in FIG. 8) or other resistant means to prevent unintended premature separation of the needle guard 122 from the support 1624. Obviously, the valve opener shown in FIGS. 7 and 8 may be usable with any of the catheter assemblies disclosed elsewhere herein having a valve.

Figure 9:
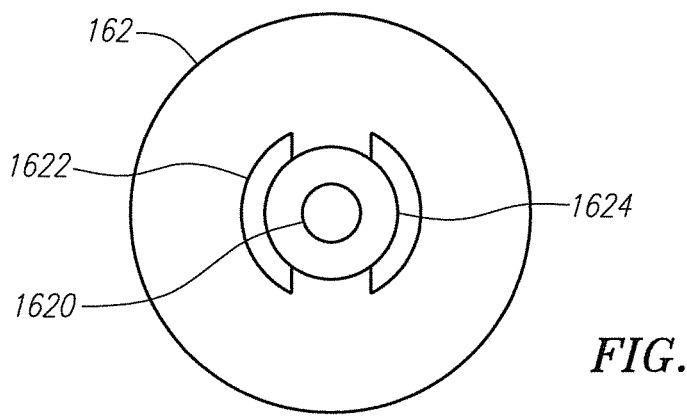
FIGS. 9-11 are various end views looking proximal to distal of embodiments of a valve opener.

Referring now to FIG. 9, an end view of a valve opener 162 provided in accordance with aspects of the present disclosure is shown, which has a support 1624 embodied as a ring like structure located between two extensions 1622 and formed around the opening 1620 of the valve opener 162. The space between the two extensions 1622 allows the ends 138, 140 of the needle guard 122 to be located there and over the support 1624 in a ready to use position, similar to that shown in FIGS. 7 and 8.

Figure 10:
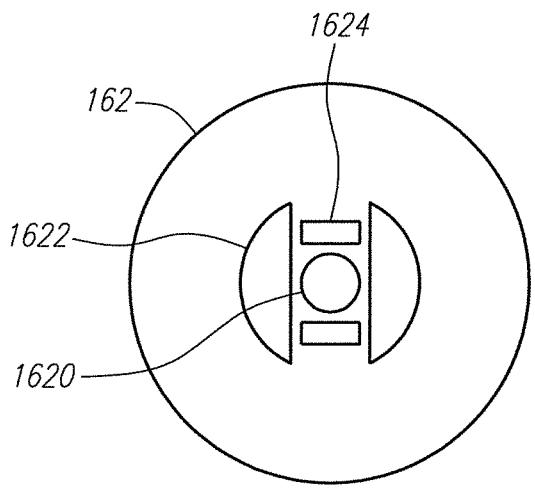

With reference now to FIG. 10, an end view of a valve opener 162 provided in accordance with further aspects of the present disclosure is shown, which has a support 1624 embodied as two or more separate sections, such as two or more ribs, formed around the opening 1620 of the nose section of the valve opener 162. The two or more ribs can be generally rectangular, arc shape, or combinations thereof. The support 1624 can have a mating surface for the ends 138, 140 of the needle guard 122 to rest thereon in a ready to use position.

Figure 11:
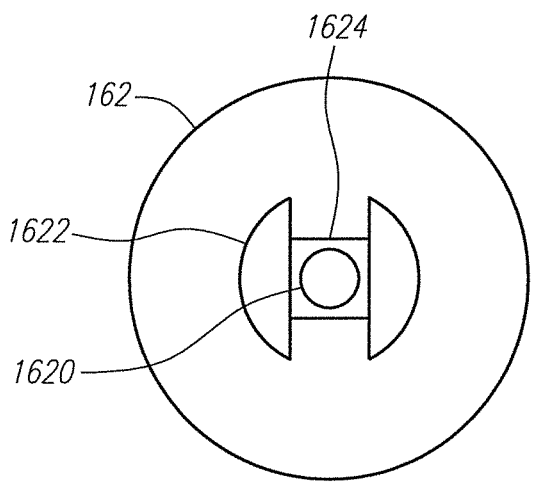

FIG. 11 is an end view of a valve opener 162 provided in accordance with still yet further aspects of the present disclosure, which has a support 1624 formed by a generally square shape stub connecting a distal portion of the two extensions 1622. The depth of the square shape stub determines the height of the support 1624. Alternatively, the support 1624 can have a flat surface to engage with the ends 138, 140 of the needle guard 122.

Although limited embodiments of the safety needle assemblies and their components have been specifically described and illustrated herein, many modifications and variations will be apparent to those skilled in the art. Furthermore, elements and features expressly discussed for one embodiment but not for another may equally apply provided the functionality or structures do not conflict. Thus, unless the context indicates otherwise, like features for one embodiment are applicable to another embodiment. Accordingly, it is to be understood that the safety needle assembly and their components constructed according to principles of the disclosed devices, systems, and methods may be embodied other than as specifically described herein. The disclosure is also defined in the following claims.

What is claimed is:

1. A safety catheter assembly comprising:
   a catheter hub comprising an interior cavity;
   a valve and a valve opener having a nose section sized and shaped for pushing into the valve to open one or more slits of the valve, said valve and said valve opener being located in the interior cavity of the catheter hub;
   a catheter tube attached to the catheter hub;
   a needle hub;
   a needle attached to the needle hub and projecting through the catheter tube and having a needle tip extending out of a distal end of the catheter tube in a ready to use position;
   a needle guard positioned in the interior cavity of the catheter hub;
   wherein the needle guard comprises a proximal wall having an opening and two arms each comprising an end;
   wherein a support is formed with the valve opener and wherein the two ends of the two arms on the needle guard rest on surfaces of the support; and
   wherein the support spaces the two ends of the two arms of the needle guard from the needle in the ready to use position so as to reduce drag between the needle and the needle guard when the needle retracts from the catheter tube and the catheter hub following vascular access.

2. The safety catheter assembly of claim 1, wherein the support is ring shaped and the support is coaxially disposed with the catheter tube.

3. The safety catheter assembly of claim 1, wherein the valve opener is slidably disposed in the interior cavity of the catheter hub to open the valve.

4. The safety catheter assembly of claim 1, wherein the two arms of the needle guard cross each other forming a cross-section and the support is spaced from the cross-section.

5. The safety catheter assembly of claim 1,
   wherein the needle comprises a change in profile located proximal of the needle tip; and
   wherein the change in profile abuts against the proximal wall of the needle guard before the needle guard separates from the support.

6. The safety catheter assembly of claim 1, wherein the valve opener comprises at least one leg.

7. The safety catheter assembly of claim 1, wherein the support has a body with a ring shape, is a stub with a bore, is formed from two or more ribs, or is a square shape stub.

8. A safety catheter assembly comprising:
 a catheter hub comprising an interior cavity;
 a valve having one or more slits and a valve opener having a nose section sized and shaped for opening the valve, said valve and said valve opener being located in the interior cavity of the catheter hub;
 a catheter tube attached to the catheter hub;
 a needle hub;
 a needle attached to the needle hub and projecting through the catheter tube in a ready to use position, said needle having a needle tip and a shaft;
 a needle guard positioned in the interior cavity of the catheter hub;
 wherein the needle guard comprises a proximal wall having a perimeter defining an opening and two arms each comprising an end;
 wherein a support interacts with the needle guard and the two ends of the two arms of the needle guard rest on the support and the support biases the two ends away from the needle in the ready to use position so as to reduce drag between the needle and the needle guard when the needle retracts from the catheter tube and the catheter hub following vascular access; and
 wherein the support is formed with the valve opener and the valve opener is located in the interior of the catheter hub, and wherein the support is spaced from the opening of the proximal wall of the needle guard in the ready to use position and in a protective position, the needle tip being blocked from inadvertent needlestick in the protective position.

9. The safety catheter assembly of claim 8, wherein the two arms of the needle guard are separated from the support when in the protective position.

\* \* \* \* \*